United States Patent [19]

Marten et al.

[11] 4,125,769

[45] Nov. 14, 1978

[54] APPARATUS FOR QUANTITATIVE IN-LINE X-RAY FLUORESCENCE ANALYSIS OF SLURRIES

[75] Inventors: Rainer Marten; Harald Schneider, both of Geesthacht, Fed. Rep. of Germany

[73] Assignee: Gesellschaft fur Kernenergieverwertung in Schiffbau und Schiffahrt mbH, Geesthacht-Tesperhude, Fed. Rep. of Germany

[21] Appl. No.: 798,121

[22] Filed: May 18, 1977

[51] Int. Cl.² ............................................. G01M 23/22
[52] U.S. Cl. .................................. 250/272; 250/277 R
[58] Field of Search ........... 250/272, 273, 274, 277 R, 250/278, 279

[56] References Cited

U.S. PATENT DOCUMENTS

| | | | |
|---|---|---|---|
| 3,443,092 | 5/1969 | Carr-Brion | 250/277 R |
| 3,795,807 | 3/1974 | Johnson | 250/277 R |
| 3,925,661 | 12/1975 | Carr-Brion | 250/272 |

*Primary Examiner*—Craig E. Church
*Attorney, Agent, or Firm*—Walter Becker

[57] ABSTRACT

An apparatus for the quantitative in-line X-ray fluorescence analysis of slurries by means of a radioactive preparation, e.g. Cd-109, and an X-ray fluorescence detector. The apparatus comprises a substantially vertical measuring tube with inlet and outlet for the slurries to be investigated, and a measuring station. Above the measuring station which contains the radioactive preparations and the fluorescence detector there is provided a filling level control which controls the state of opening of the outlet.

8 Claims, 3 Drawing Figures

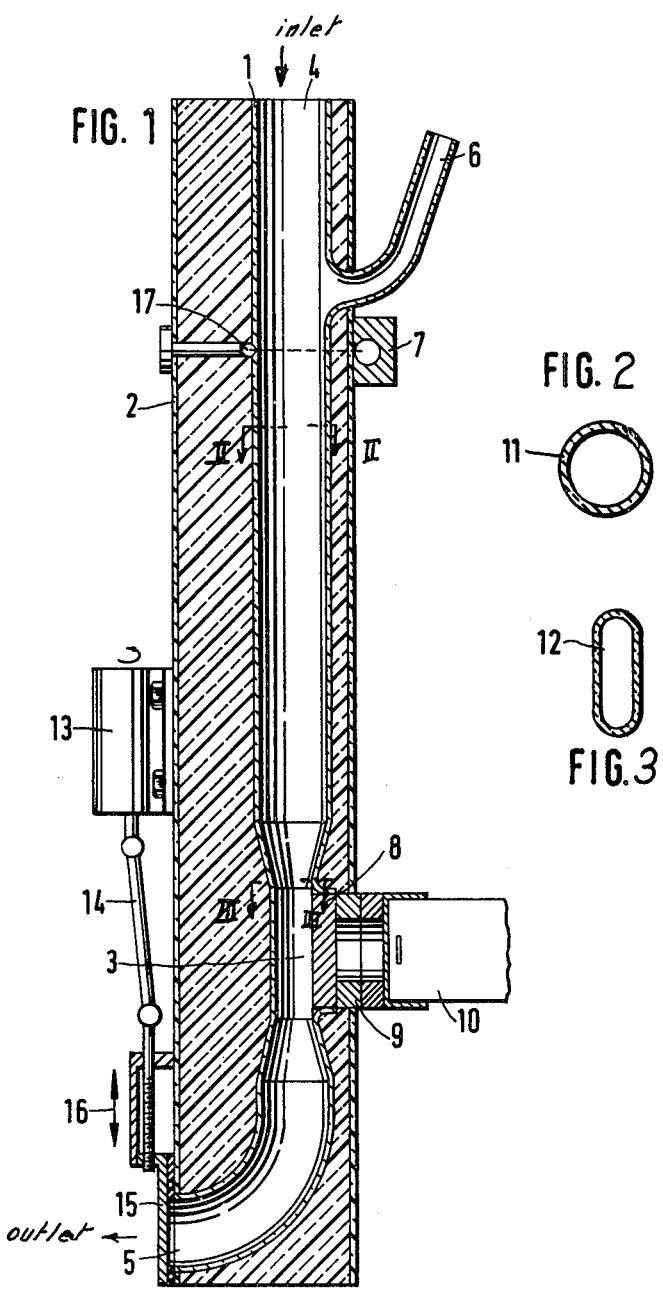

APPARATUS FOR QUANTITATIVE IN-LINE X-RAY FLUORESCENCE ANALYSIS OF SLURRIES

The present invention relates to a device for quantitative in-line X-ray fluorescence analysis of slurries by means of a radioactive preparation and an X-ray fluorescence detector.

In practice it frequently occurs that with slurries, as for instance water-sand mixtures, to be checked, which are supplied continuously or in batches, the water content of the samples varies. Heretofore it has been difficult to evaluate such slurry samples by means of a quantitative X-ray fluorescence analysis because for this purpose a relatively constant water component of the slurry or homogeneous precisely defined surface has to be present within the measuring region.

It is, therefore, an object of the present invention to provide a device for quantitative X-ray fluorescence analysis of slurries or the like which is structurally simple and which excels by high measuring precision.

It is another object of this invention to provide a device as set forth in the preceding paragraph, which will permit a continuous measuring, even when the slurry samples are supplied in batches or stepwise.

These and other objects and advantages of the invention will appear more clearly from the following specification in connection with the accompanying drawing in which:

FIG. 1 diagrammatically illustrates partially in section the essential structural elements of a device according to the present invention.

FIGS. 2 and 3 respectively illustrate sections along the lines II—II and III—III of FIG. 1.

The device according to the present invention is characterized primarily in that in a substantially vertically arranged measuring tube with inlet and outlet for the slurries or the like to be checked there is above the measuring station with the radioactive preparation and a fluorescence detector provided a filling level control which controls the opening condition of a closing valve arranged below said measuring station.

The slurry samples which, as the case may be, may be delivered in batches or stepwise, are thus introduced from above into the inlet of the measuring tube while first the closing valve is closed. As soon as a sufficient sample volume has accumulated in the measuring tube so that the filling level control responds, the latter through a signal emanated therefrom opens the closing valve in conformity with a previously determined control characteristic. The samples in the measuring tube then flow past the measuring station and are there analyzed. To this end, a window, e.g. a berylium window, permeable for the employed X-rays, is provided in the wall of the measuring tube and in the region of said measuring station. As a result thereof, the required precisely defined surface of the slurry to be checked is assured within the region of the measuring station. Depending on the volume of the then obtained slurry samples, the opening condition of the closing valve is, while being controlled again by means of the filling level control, so adjusted that a continuous measuring operation of the respective obtained slurries will be possible.

A structurally particularly simple embodiment of the device according to the invention is characterized in that the closing valve is designed as shut-off valve which latter is actuated by a servo motor. An arrangement is preferred according to which above the filling level control and overflow pipe leads into the measuring tube. By means of said overflow pipe it is possible to control the pressure at the inlet, to discharge excess water or to feed in additional liquid.

Referring now to the drawing in detail, a measuring tube 1 is arranged in a housing 2 of acrylic glass which housing 2 is filled with transparent silicon rubber. The measuring tube 1 is arranged substantially vertically. Its cross section remains substantially unchanged up to the region of the measuring station 3. Below the measuring station 3, the measuring tube 1 is laterally bent into a horizontal plane. As a result thereof, the measuring tube is at its upper end provided with an inlet 4 and at its lower end with an outlet 5.

Below the inlet 4 an overflow pipe 6 leads into the measuring tube 1. Directly below the mouth of the overflow pipe 6 there is provided a filling level control 7 which may contain a radioactive preparation, e.g. Cd-109, and is adapted to emit signals to a servo motor 13. The attenuation of the rays emitted by said preparation when said rays pass through the measuring tube 1 represents a measure for the filling level of said measuring tube 1. Also other heretofore known filling level controls are possible, for instance light barrier devices or photographic recorders.

The measuring station 3 is located in the lower ⅓ of the measuring tube 1. A beryllium window 8 is provided at the location of said measuring station. On the outside of said window there is provided a radioactive preparation 9, for instance Cd-109. The preparation 9 generates a radioactive radiation which passes through the beryllium window 8 and while acting upon the slurry in the tube section 3 generates X-ray fluorescence which is then through said beryllium window 8 received by a detector 10 located opposite window 8.

X-ray fluorescence detectors are known per se. With detectors of this type, X-rays are employed which, when striking a preparation to be investigated, generate a visible light in a fluorescence layer, which light can be measured by means of photometers or photomultipliers.

The preparation 17, which may be of the same type as the preparation 9, together with the filling level control or the radiation receiver 7 forms an indicator for the filling of tube 1. Since the measuring tube 1 is not light permeable, a customary light barrier with light source and photoelectric cell cannot be used in this connection. It is for this reason that for penetration of the wall of tube 1 and the tube filling, a radioactive radiation is employed. The degree to which much or little radiation is received will indicate whether the tube 1 is or is not filled in the measuring plane. Such filling level control basically operates like light barrier controls with visible light and photoelectric cell employed with self-opening doors which are kept open as long as a person is in the path of the light beams; only in the present case radioactive radiation is employed for the above-mentioned reasons.

The cross section of the measuring tube 1 is normally circular, as indicated in the position 11 of FIG. 2. Within the region of the measuring station 3, the cross section 12 is flattened as shown in FIG. 3. In this way, a measuring volume is designed which is in conformity with the X-ray fluorescence detector 10.

The emitted signals of the filling level control 7 pass onto a servo motor 13 which through the intervention of a drive shaft 14 is connected to a shut-off valve 15. In this way, the outlet 5 of the measuring tube 1 is opened more or less in conformity with the filling level measured by the filling level control 7. To this end, the servo motor 13 moves the shut-off valve in the direction of the double arrow 16. By suitable selection of the control characteristic of the shut-off valve, a continuous flow of material in conformity with the delivered quantity of the sample is adjusted by the measuring volume, which flow of material meets the essential requirements for the application of the X-ray fluorescence analogue method, namely a smooth bubble-free surface in front of the beryllium window 8, no marginal layers of the sample material becoming stuck at the limiting surface 11, and constant water content. The term "limiting surface" designates the bubble free surface of the Beryllium window which is contacted by the passing-by slurry.

It is, of course, to be understood that the present invention is, by no means, limited to the specific showing in the drawing, but also encompasses any modifications within the scope of the appended claims.

What we claim is:

1. An apparatus for the quantitative in-line X-ray fluorescence analysis of slurries, which includes: a measuring tube having an inlet and an outlet for respectively receiving the slurries to be investigated and releasing investigated slurries, a measuring station arranged at an area of said measuring tube which area is located between said inlet and said outlet, said measuring station including a radioactive preparation for generating X-ray fluorescence radiation through the slurry at said measuring station and also including a detector for receiving and measuring said fluorescence radiation through said slurry at said measuring station, filling level control means arranged at said tube between said inlet and said measuring station for controlling the filling level of said tube, a control valve arranged at said outlet and operable to vary the free opening of said outlet, and servo-motor means operatively connected to said control valve, said filling level control means being operatively connected to said servo-motor means to cause the latter to actuate said control valve in conformity with a predetermined filling level of said slurry in said tube.

2. An apparatus according to claim 1, in which said filling level control means is operable to send signals to said servo-motor means, and in which said servo-motor means is operable in response to said signals to actuate said control valve.

3. An apparatus according to claim 1, which includes an X-ray permeable window in the wall of said tube within the region of said measuring station and in the path of the rays emitted by said preparation.

4. An apparatus according to claim 3, in which said window is a beryllium window.

5. An apparatus according to claim 1, in which said tube is arranged in a housing surrounding said tube in spaced relationship thereto so as to define therewith an annular chamber, said housing consisting of acrylic glass (Acryl-glas), and said annular chamber being filled with silicon rubber.

6. An apparatus according to claim 1, in which said control valve is a shut-off valve.

7. An apparatus according to claim 1, which includes an overflow pipe leading into said tube between said filling level control means and said inlet.

8. An apparatus according to claim 1, in which the measuring volume of said measuring tube within the region of said detector is designed in conformity with the latter.

* * * * *